United States Patent
Azar et al.

(10) Patent No.: US 8,506,626 B2
(45) Date of Patent: Aug. 13, 2013

(54) TRANSCORNEAL VISION ASSISTANCE DEVICE

(75) Inventors: Dimitri Azar, Chicago, IL (US); Jose De La Cruz, Chicago, IL (US); Sandeep Jain, Oak Park, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 470 days.

(21) Appl. No.: 12/600,967

(22) PCT Filed: Mar. 13, 2008

(86) PCT No.: PCT/US2008/003334
§ 371 (c)(1),
(2), (4) Date: Jan. 5, 2010

(87) PCT Pub. No.: WO2008/150319
PCT Pub. Date: Dec. 11, 2008

(65) Prior Publication Data
US 2010/0168849 A1 Jul. 1, 2010

Related U.S. Application Data

(60) Provisional application No. 60/931,632, filed on May 24, 2007.

(51) Int. Cl.
*A61F 2/14* (2006.01)

(52) U.S. Cl.
USPC .......................... 623/5.14; 623/5.11

(58) Field of Classification Search
USPC .................................. 623/5.11–5.16
See application file for complete search history.

(56) References Cited

U.S. PATENT DOCUMENTS

| | | | | |
|---|---|---|---|---|
| 4,470,159 | A * | 9/1984 | Peyman | 623/5.11 |
| 5,133,747 | A * | 7/1992 | Feaster | 623/6.34 |
| 6,066,171 | A * | 5/2000 | Lipshitz et al. | 623/6.18 |
| 2005/0129735 | A1* | 6/2005 | Cook et al. | 424/423 |
| 2007/0067030 | A1* | 3/2007 | Glazier et al. | 623/6.13 |

FOREIGN PATENT DOCUMENTS

RU 2139014 * 10/1999

* cited by examiner

*Primary Examiner* — David H Willse
*Assistant Examiner* — Tiffany Shipmon
(74) *Attorney, Agent, or Firm* — Greer, Burns & Crain Ltd.

(57) ABSTRACT

The invention provides a transcorneal vision assistance device implantable in the eye of a patient. A preferred embodiment transcorneal microtelescope vision assistance device is implantable in the eye of a patient and includes a keratoprosthesis configured to replace a portion of the cornea of a patient and to secure the keratoprosthesis to a remaining front portion of the cornea. A microtelescope is carried by the keratoprosthesis for transcorneal mounting of the microtelescope.

14 Claims, 4 Drawing Sheets

TRANSCORNEAL VISION ASSISTANCE DEVICE

REFERENCE TO RELATED APPLICATION AND PRIORITY CLAIM

This application claims priority under 35 U.S.C. §119 from prior provisional application Ser. No. 60/918,509, filed Mar. 16, 2007 and from prior provisional application Ser. No. 60/931,632, filed May 24, 2007.

FIELD

A field of the invention is vision assistance, particularly artificial, surgically implantable vision assistance devices.

BACKGROUND

As elderly populations increase, there is a marked increase in the occurrence of debilitating eye diseases. Common diseases include Advanced Age Related Macular Degeneration, Glaucoma, Diabetic Retinopathy and Cataracts. All of these diseases can lead to severe vision loss and blindness. Macular degeneration is the leading cause of all blindness. The macula is a specialized region in the center of the retina that provides detailed central vision. Macular degeneration typically produces a severe vision loss in the central field of view of an individual.

Technology struggles to provide assistance to advanced stages of disease. External visual aids can provide assistance to patients with severe vision loss. However, external visual aids have restricted functionality. External magnifying glasses and external telescopes provide narrow fields of view. Such external aids also tend to be cumbersome and aesthetically unappealing.

Significant efforts have also been directed toward providing surgical solutions to aid vision in the case of severe vision loss and/or blindness. One approach that has been investigated to address severe vision disabilities is an implantable telescope. U.S. Pat. No. 6,596,026, for example, describes an implantable miniature telescope. Additional variations are described in U.S. Pat. Nos. 5,354,335; 5,391,202; 5,814,103; 5,876,442; 5,928,283; 6,007,579 and 6,066,171. Implantable telescopes can be Galilean and can correct central field defects.

Vision Care Ophthalmic Technologies has produced prototype implantable telescope devices to correct for central field defects. The telescope is referred to the implantable miniature telescope. The implantable miniature telescope is, at the time of filing of this application, currently in the process of clinical studies. The implantable miniature telescope is configured for implantation in the posterior capsular bag, taking the place of the eye's crystalline lens. It consists of two microlenses arranged to magnify, by 2.2× or 2.7× nominal magnification the central visual field of a patient's vision. The is device is a prosthetic telescope and acts in cooperation with the patient's cornea to provide enlarged images. Wide and normal models having 3× or 2.2× (2.7 or 2.2× nominal) magnification have been developed. With the magnification provided by the telescope, images in the central visual field can be focused over other healthy areas of the central and peripheral retina.

The implantable miniature telescope has a number of disadvantages. Initial FDA testing has revealed safety concerns with the implantable telescope. The FDA, in a Jul. 14, 2006 Panel Meeting Summary of the Ophthalmic Devices Panel found that testing of the implantable miniature telescope did not provide reasonable assurance that the device was safe. A major safety concern identified by the panel was endothelial cell density loss.

Problems of the implantable miniature telescope and the likely causes of the problems have been identified and are addressed by the present invention. The surgical solution for the implantable miniature telescope involves a surgical entrance through the side of the eye. This approach is borrowed from cataract surgery, and comes with the problems associated with cataract surgery.

A haptic ring mounts the device in a capsular bag placement. This position may shift with time, causing problems with maintaining central position of the device. Central position is critical to maintaining the beneficial effect of the telescope, and stability is critical to maintaining healthy tissue. Additionally, the position relative to the cornea is not stable and movement toward the cornea can cause injury to endothelial cells and lead to corneal decompensation. Damage caused to the cornea is contradictory to the necessary eye condition to obtain benefit of the telescope. Implantation is not considered even in the clinical studies for patients having levels of cornea opacity, decreased endothelial cell count, or a compromised capsular bag.

The instability in addition to the materials and configuration of the haptic ring may also be the cause of the endothelial tissue losses experienced in clinical studies. The telescope relies upon a transparent cornea, and its application requires a healthy cornea to begin with.

A separate area of research concerns cornea opacities. Cornea issues have been considered separately from the retinal issues. The primary model for cornea repair is donor corneal tissue. For cases of repeated corneal graft rejection, Keratoprosthesis (artificial cornea) devices have been investigated. Examples are disclosed in U.S. Pat. Nos. 4,923,466; 4,586,929; 5,300,116; 5,458,819; 5,843,185; 5,354,332, and 4,470,159. The model for such a device has been the replacement of the diseased cornea with an artificial one. Several devices have been implanted and studied. Donor corneal tissue remains the favored approach.

SUMMARY OF THE INVENTION

The invention provides a transcorneal vision assistance device implantable in the eye of a patient. A preferred embodiment device includes a front plate having an artificial cornea. A microtelescope away from the artificial cornea and is optically aligned with the central portion of the artificial cornea. Corneal tissue forms a peripheral part of the artificial cornea that can be sutured to the front of portions of a cornea of a patient. A back plate is configured to conform to the back of portions of the cornea of a patient. The back plate includes sufficient open areas or holes to promote continued health of tissue and nutrient flow. A locking ring mounts the device fixedly to the back of the cornea in cooperation with the back plate.

A preferred embodiment transcorneal microtelescope vision assistance device is implantable in the eye of a patient. The device includes a keratoprosthesis configured to replace a portion of the cornea of a patient and to secure the keratoprosthesis via corneal tissue to a remaining front portion of the cornea. A microtelescope is carried by the keratoprosthesis for transcorneal mounting of the microtelescope.

Another preferred embodiment, transcorneal vision assistance device includes a front plate having an artificial cornea. Corneal tissue forms a peripheral part of the artificial cornea that can be sutured to the front of portions of a cornea of a patient. A back plate is configured to conform to the back of portions of the cornea of a patient, the back plate including a central ring and collapsible arms that extend away from the central ring when opened.

DETAILED DESCRIPTION OF THE PREFERRED EMBODIMENTS

Figure 1:
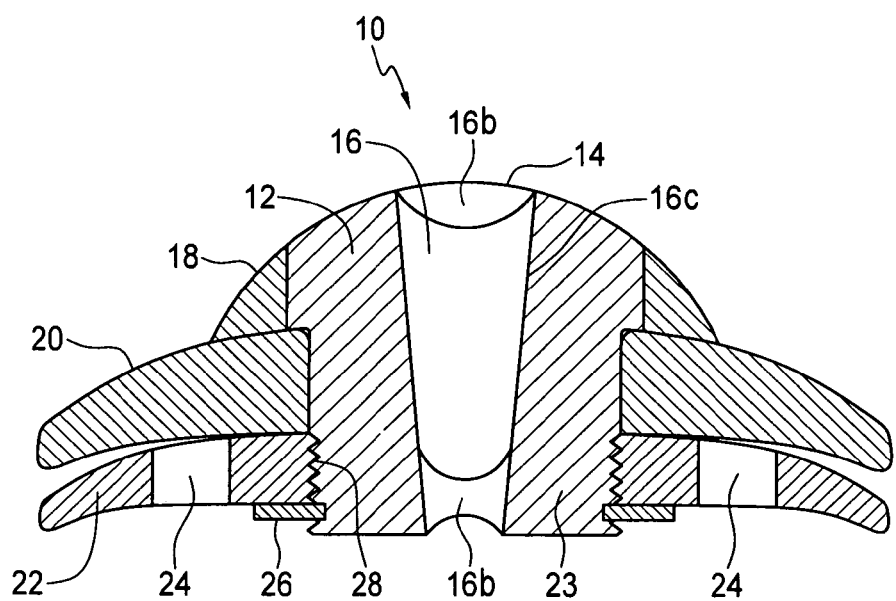
FIG. 1 is a schematic cross-sectional view of a preferred embodiment transcorneal microtelescope vision assistance device that is implanted in the eye of a patient.

Devices of the invention are transcorneal, i.e., through the cornea, implantable telescope devices. An artificial cornea lens replaces a central part of a patient's cornea and provides a clear optical path through the cornea of an eye into which the telescope device is implanted. The position of the device in the eye provides greater range of magnification as the telescope is positioned at the patient's cornea. Additionally, the position and mounting capabilities of the device make it stable, i.e., its position will be maintained within the eye.

The invention overcomes a reluctance to consider replacement of a healthy cornea to correct vision problems concerning the retina, such as macular degeneration. Prior to the invention, others have and continue to believe that a healthy or mostly healthy cornea must be left in its state. Devices of the invention, seeking to improve vision unrelated to cornea problems, replace a part of a cornea with an artificial cornea that is part of an integrated implantable telescope device. Modern keratoprosthesis devices having donor tissue to suture to the cornea have successfully reduced the number of complications and the artificial cornea devices and now show promise for replacement of damaged corneas in cases of repeated corneal graft failure. The invention recognizes a benefit of replacing a healthy cornea portion with a prosthesis to address vision problems unrelated to cornea health.

An embodiment of invention provides a transcorneal microtelescope vision assistance device implantable in the eye of a patient. A preferred embodiment device includes a front plate having an artificial cornea. A microtelescope extends away from the artificial cornea within the front plate and is optically aligned with the central portion of the artificial cornea. Corneal tissue forms a peripheral part of the artificial cornea that can be sutured to the front of portions of a cornea of a patient. A back plate is configured to conform to the back of portions of the cornea of a patient. The back plate includes sufficient open areas or holes to promote continued health of tissue and nutrient flow. A locking ring mounts the device fixedly to the back of the cornea in cooperation with the back plate.

A preferred embodiment transcorneal microtelescope vision assistance device is implantable in the eye of a patient. The device includes a keratoprosthesis configured to replace a portion of the cornea of a patient and to secure the keratoprosthesis via corneal tissue to a remaining front portion of the cornea. A microtelescope is carried by the keratoprosthesis for transcorneal mounting of the microtelescope.

A preferred embodiment device is an implantable microtelescope. A lens, such as a PMMA lens coupled with some corneal tissue is sized and shaped to replace part of the cornea of an eye into which the device is implanted. The corneal tissue is configured around the artificial cornea, carrier of the miniature telescope, for use as a suture to the remaining part of a cornea into which the device will be implanted. A microtelescope, e.g., a Galilean telescope; is attached to a back plate of the artificial cornea front plate. Another example microtelescope is a Keplerian telescope. The back plate preferably includes a number of holes and is made of PMMA or titanium. The holes are designed and configured to permit tissue life and nutrient flow around the back plate and nutrient flow through and around the back plate. The corneal mount location of the telescope provides the opportunity for significant magnification, e.g., of 3-5× and up to 6×. The transcorneal mount also provides stability, and reduces the risks associated with an unstable position within the eye. The device provides an air-lens interface instead of a fluid-lens interface (as in a capsular bag placed telescope), proving a favorable difference in the indices of refraction.

A preferred embodiment device includes a front plate having an artificial cornea. A microtelescope extends away from the artificial cornea and is optically aligned with the central portion of the artificial cornea. Corneal tissue forms a peripheral part of the artificial cornea and can be sutured to the cornea of a recipient of the device. A back plate includes sufficient open areas or holes to promote continued health of surrounding tissue, and fixes the telescope position to the cornea. A locking ring, preferably of titanium, mounts the device fixedly to the back of the cornea in cooperation with the back plate.

Preferred embodiments of the invention will now be discussed with respect to the drawings. The drawings may include schematic representations, which will be understood by artisans in view of the general knowledge in the art and the description that follows. Features may be exaggerated in the drawings for emphasis, and features may not be to scale.

Figure 2A:
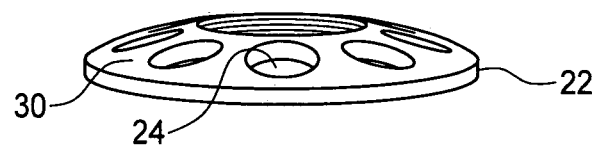
FIG. 2A is a perspective view and FIG. 2B a top view of a back plate of the preferred embodiment microtelescope vision assistance device of FIG. 1.
Figure 2B:
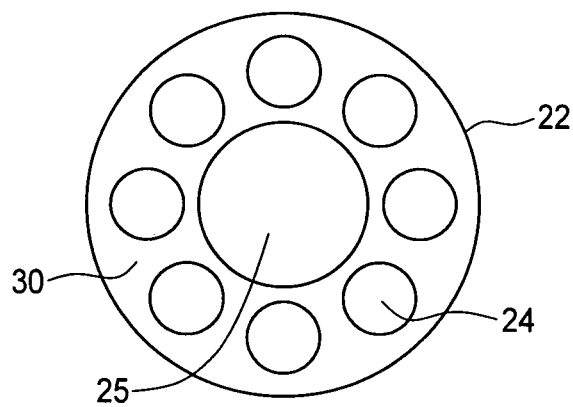

FIGS. 1-2B illustrates a preferred embodiment transcorneal microtelescope vision assistance device 10 that is implanted in the eye of a patient. The transcorneal microtelescope device 10 includes a front plate 12 having an artificial cornea 14. The artificial cornea 14 forms a lens, and can be made, for example, of PMMA. A microtelescope 16 extends away from the artificial cornea 14 and is optically aligned with the central portion of the artificial cornea. The microtelescope includes lenses 16a and 16b with an air bubble between. The lens 16a can form part of the artificial cornea 14. The lenses 16a and 16b are spaced and shaped to achieve a desired magnification, e.g., 5×. The microtelescope is hermetically sealed in a housing 16c.

U.S. Pat. No. 4,074,368 discloses a Galilean telescope, with optics and materials that are suitable for use in devices of the present invention. Various magnification powers can be achieved by the curvatures of the lenses 16a, 16b, the space between them, and the gas used as bubbles between the lenses. Another example microtelescope is described, for example, in U.S. Pat. No. 6,596,026. The materials and general construction of the optics and their housing of the telescope in U.S. Pat. No. 6,596,026 can also be used for the microtelescope 16 of the invention. However, the transcorneal position of the present microtelescope permits the optics to be shaped for significant magnification, e.g. up to 6×, with changed optics. Additional microtelescopes are described in U.S. Pat. Nos. 5,354,335; 5,391,202; 5,814,103; 5,876,442; 5,928,283; 6,007,579 and 6,066,171.

Corneal tissue 18, such as donor tissue or corneal tissue taken from a patient in which the device will be installed, forms a peripheral part of the artificial cornea that can be sutured to the front of portions of a cornea 20 of a patient. A back plate 22 is configured to conform to the back of portions of the cornea 20 of a patient and accommodate an extension 23 of the front plate 12. The back plate 22 and front plate with the artificial cornea form a keratoprosthesis that securely holds the microtelescope 16 by securing it to both the back and front of a patients cornea. The back plate 22 includes sufficient open areas or holes 24 to promote continued health of corneal tissue and nutrient flow. The extension 23 contains the microtelescope 16 and extends into a central opening 25 (best seen in FIG. 2B) of the back plate 22. A locking ring 26, for example a titanium ring, mounts the device fixedly to the back of the cornea 20 in cooperation with the back plate 22. As seen in the preferred embodiment of FIG. 1, the front plate 12 extends axially through the cornea 20 and preferably makes a threaded connection 28 with the opening 25 of the back plate 22 and/or the locking ring 26.

Instead of the locking ring, features on the front plate 12, back plate 22, extension 23, etc. can be configured with bumps and grooves or other features such that the front plate 12 and 22 plate lock together upon installation without need for a locking ring 26. Various mechanical interfaces can be used to create a stable interconnection of the front and back parts of the device during surgical installation. Additionally, a large diameter front plate 12 may provide sufficient stability for serving as the Keratoprosthesis part of the device to obviate the need for a back plate. Large diameter "contact lens" style artificial corneas, suture and glue techniques are other types of artificial cornea solutions can be modified for the trancorneal telescope mount of the invention. As an example. Lenart et al., "A Contact Lens as an Artificial Cornea for Improved Visualization During Practice Surgery on Cadaver Eyes"; Arch Opthalmol. Vol. 121: pp. 16-19 (2003), provides another type of Keratoprosthesis the uses a wide front mount "contact lens" of PMMA and glue.

FIGS. 2A and 2B illustrate the back plate 22 of FIG. 1. The holes 24 provide for nutrient flow, and preferably are as large as possible. The size of the holes 24 relative to the solid surfaces of the back plate 22 is limited only by the need to maintain sufficient structural integrity of the back plate 22 to hold the vision assistance device in a stable position. As best seen in FIG. 2A, an upper surface 30 of the back plate 22 forms a semi-spherical surface to mimic the back of the cornea 20.

The front plate 12 and back plate 22 are of the form of the Boston Keratoprosthesis Type I. Keratoprosthesis devices are disclosed in U.S. Pat. Nos. 4,923,466; 4,586,929; 5,300,116; 5,458,819; 5,843,185; 5,354,332, and 4,470,159. Instead of the clear lens insert used in such devices, the to microtelescope 16 is used in the invention. The surgical procedure to install the device 10 of FIGS. 1-2B follows that of the installation of the Boston Keratoprosthesis Type I. The central part of the cornea 20 is removed, and the device 10 is then sutured into the patient's cornea.

Figure 3A:
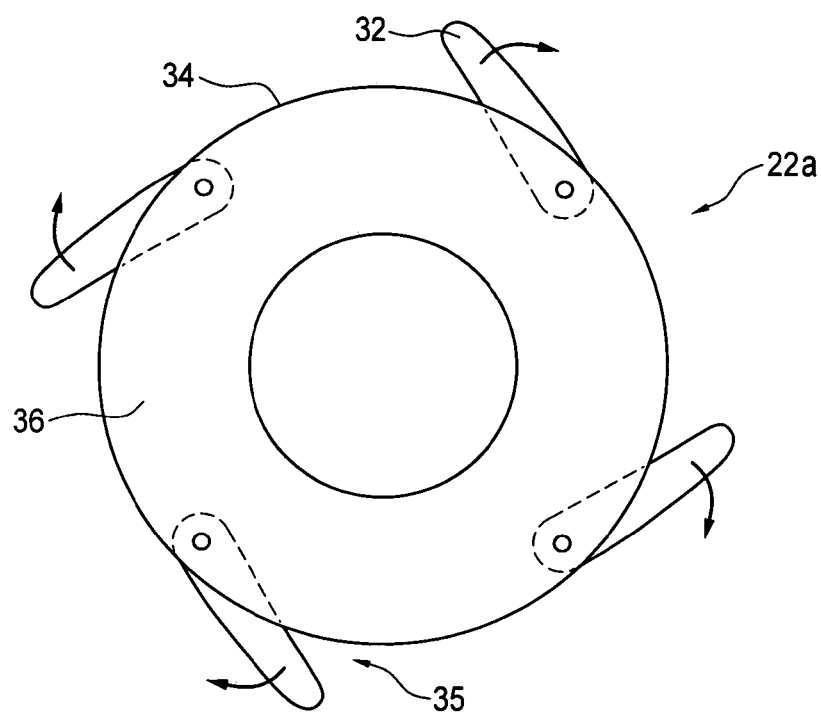
FIGS. 3A and 3B illustrate an alternate back plate for a preferred embodiment microtelescope vision assistance device.
Figure 3B:
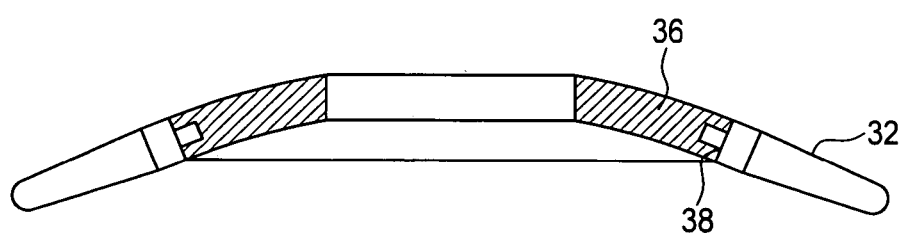

The back plate 22 in the FIGS. 1-2B device 10 can be replaced with other plates that have sufficient mechanical integrity to hold the device 10 in a very stable position relative to the cornea 20 while also allowing sufficient nutrient flow to the cornea. Collapsible structures are possible. FIGS. 3A and 3B illustrate a back plate 22a that makes use of collapsible arms 32 that can be extended and locked into an extended position (see FIG. 3B) during surgical installation. Advantages of such a back plate 22a include a reduction of the amount of surface area necessary to secure the fixed, stable position of the device 10 relative to the back of the cornea 20 and a smaller incision necessary for surgical installation of the device 10 or of a keratoprosthesis like the device 10 but lacking the microtelescope. The smaller surface area can obviate the need for the holes used in FIGS. 1-2B. The back plate 22 in FIGS. 1-2B has the advantage of providing more surface contact to the back of the cornea 20 and can possibly be the most stable arrangement.

The back plate 22a includes a central ring 34 with a smaller surface area 36 than the surface 30 of the back plate 22. The central opening 25 that accepts the extension 23 of the front plate 12 is the same as the back plate 22, e.g., 3 mm. However, the width of solid portions that make up the surface 30 of the ring 34 can be smaller, e.g., 1 mm, than the back plate 22. The arms 32, when extended, can add another 1.5 mm, for example, and follow a curve in the surface 30 to mimic the semi-spherical shape of the back of the cornea 20. Open areas 35 between the arms provided sufficient nutrient flow to keep the cornea 20 healthy as the central ring 34 provides a comparatively small amount of surface to cornea contact. A locking mechanism 38, e.g., a detent on the surface 30 or a locking hinge, cooperates to lock the arms 32 into place after installation.

The surgical procedure to install a device of the invention to including the FIGS. 3A and 3B back plate 22a is as follows. The foldable back plate 22a is inserted through a limbal incision. A central part of the patient's cornea is then removed. The extension 23 of the front plate (which has the microtelescope pre-installed or has no a plain lens if the surgical goal is merely to remove a corneal opacity) is then inserted through the central part of the cornea and through the central opening 25. The back plate is held with a holder through the limbal incision. The arms 32 are extended and locked into place. A locking ring (see FIGS. 1-2B) locks the back plate 22a in place on the extension once properly positioned. The limbal incision is closed, and the corneal tissue is used to suture the front plate to the front of the cornea.

Figure 4A:
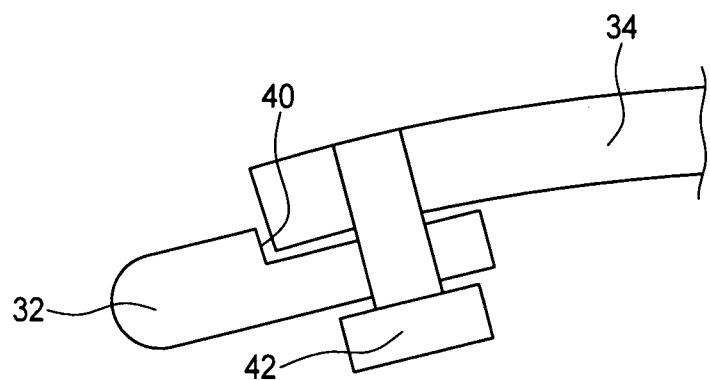
FIGS. 4A and 4B is a partial schematic view of respective extended and retracted positions of an arm relative to the back plate of FIGS. 3A and 3B.
Figure 4B:
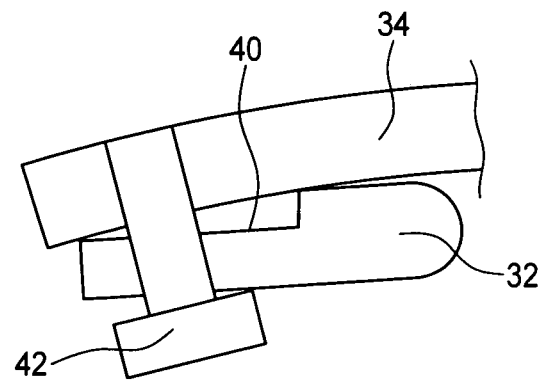

FIGS. 4A and 4B show respective extended and retracted positions of an arm 32 relative to the central ring 34. A locking mechanism is achieved in the example of FIGS. 4A and 4B with the use of material flexibility and a ridge 40 on the arms 32. In the closed position of FIG. 4B, a pin 42 provides sufficient tension to slightly bend a far end of the arm against the central ring 34. When folded open, as in FIG. 4A, the arm 32 snaps into a fixed position against a side of the central ring 34. The FIGS. 3A-4B back plates can also be used as an improved artificial cornea device with the configuration of FIG. 1 where the microtelescope 16 is omitted.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. A transcorneal microtelescope vision assistance device implantable in the eye of a patient, the device comprising:
    a front plate having an artificial cornea, the front plate being configured to extend axially through a cornea and being dimensioned to replace only a central portion of a patient's cornea;
    a microtelescope held by and within the front plate, the microtelescope being held in a portion of the front plate extending away from the artificial cornea and being optically aligned with the central portion of the artificial cornea;

corneal tissue forming a peripheral part of the artificial cornea that can be sutured to the front of portions of a cornea of a patient;

a back plate configured to conform to the back of portions of the cornea of a patient, the back plate including sufficient open areas or holes to promote continued health of tissue and nutrient flow, the back plate and front plate being, configured to be in locked engagement with each other such that the engagement between the back plate and front plate fixes the back plate to the back of the cornea.

2. The device of claim 1, wherein the locked engagement is aided by a locking ring that locks an extension of the front plate to a backside of the back plate.

3. The device of claim 1, wherein the microtelescope provides a magnification of at least 3×.

4. The device of claim 1, wherein the microtelescope provides a magnification of 5×.

5. The device of claim 1, wherein the microtelescope is a Galilean microtelescope.

6. The device of claim 1, wherein the back plate comprises titanium.

7. The device of claim 6, wherein the back plate comprises holes to provide nutrient flow.

8. A transcorneal microtelescope vision assistance device implantable in the eye of a patient, the device comprising:

a front plate having an artificial cornea;

a microtelescope extending away from the artificial cornea and optically aligned with the central portion of the artificial cornea;

corneal tissue forming a peripheral part of the artificial cornea that can be sutured to the front of portions of a cornea of a patient; and a back plate configured to conform to the back of portions of the cornea of a patient, the back plate including sufficient open areas or holes to promote continued health of tissue and nutrient flow, wherein the back plate comprises a central ring and collapsible arms that extend away from the central ring when opened.

9. The device of claim 8, wherein each of the arms connect to the central ring by a pin that slightly deforms the arms in a closed position against a surface of the central ring when the arms are closed and allows ridge to lock the arms against a side of the central ring when the arms are opened.

10. A transcorneal microtelescope vision assistance device implantable in the eye of a patient, the device comprising:

a keratoprosthesis configured to replace a portion of the cornea of a patient and to secure the keratoprosthesis to a remaining front portion of the cornea, the keratoprosthesis comprising a front plate having an artificial cornea, the front plate being configured to extend axially through a cornea and being dimensioned to replace only a central portion of a patient's cornea;

a microtelescope carried by said keratoprosthesis for transcorneal mounting of the microtelescope, the microtelescope being held by and within the front plate, the microtelescope being held in a portion of the front plate extending away from the artificial cornea and being optically aligned with the central portion of the artificial cornea;

and a back plate configured to conform to the back portions of the cornea of a patient, the back plate including sufficient open areas or holes to promote continued health of tissue and nutrient flow, the back plate and front plate being configured to be in locked engagement with each other such that the engagement between the back plate and front plate fixes the back plate to the back of the cornea.

11. A transcorneal vision assistance device implantable in the eye of a patient, the device comprising:

a front plate having an artificial cornea;

corneal tissue forming a peripheral part of the artificial cornea that can be sutured to the front of portions of a cornea of a patient; and a back plate configured to conform to the back of portions of the cornea of a patient, the back plate including a central ring and collapsible arms that extend away from the central ring when opened.

12. The device of claim 11, wherein each of the arms connect to the central ring by a pin that slightly deforms the arms in a closed position against a surface of the central ring when the arms are closed and allows ridge to lock the aims against a side of the central ring when the arms are opened.

13. The device of claim 1, wherein the front plate and back plate lock to each other to fix the back plate to the back of the cornea.

14. The device of claim 13, wherein a portion of the front plate is in threaded engagement with the back plate.

* * * * *